United States Patent [19]
Farb et al.

[11] Patent Number: 5,539,086
[45] Date of Patent: Jul. 23, 1996

[54] THERAPEUTIC FRAGMENTS OF VON WILLEBRAND FACTOR

[75] Inventors: David L. Farb, Chalfont; Michael E. Hrinda, Gwynedd Valley; Ted C. K. Lee, Lansdale; Christopher P. Prior, Wayne, all of Pa.

[73] Assignee: Rhône-Poulenc Rorer Pharmaceuticals Inc., Collegeville, Pa.

[21] Appl. No.: 198,849

[22] Filed: Feb. 18, 1994

Related U.S. Application Data

[63] Continuation of Ser. No. 717,942, Jun. 20, 1991, abandoned.

[51] Int. Cl.⁶ .................... A61K 38/37; C07K 14/745; C07K 1/14
[52] U.S. Cl. .................... 530/383; 530/408; 530/412
[58] Field of Search ..................... 530/381, 383, 530/408, 412, 416; 514/2, 8, 12, 21; 435/69.6

[56] References Cited

U.S. PATENT DOCUMENTS

| | | | |
|---|---|---|---|
| 4,578,218 | 3/1986 | Saundry | 530/383 |
| 4,877,608 | 10/1989 | Lee et al. | 424/85.8 |
| 5,043,429 | 8/1991 | Zimmerman | 530/383 |

FOREIGN PATENT DOCUMENTS

| | | |
|---|---|---|
| 0255206 | 2/1988 | European Pat. Off. |
| 0373679 | 6/1990 | European Pat. Off. |

OTHER PUBLICATIONS

Mitraki, A. et al. *Bio/Technology* 7:690–697 (1989).
Wang et al (1988) J. Parenteral Sci & Technol. 42 (Suppl), 54–526.
Fujimura et al (1986) J. Biol. Chem. 261, 381–385.
Pietn et al (1989) Biochem Biophys Res. Comm 164, 1339–1347.
Sofen et al. (1984) BioTechnology 2, 1035–1038.
Pharmacia in "Ion Exchange Chomatography: Principles and Methods", Rahms i Lund (1983) pp. 29–35.
Mohri, H. et al., *J. Biol. Chem.*, 263(34), 17901–17904 (1988).
Oka, et al., *J. Mol. Biol.*, 147:217–226 (1981).
Barany, F., *Gene*, 37:111–123 (1985).
Williams, D. C. et al., *Science*, 215, 687–689, (1982).
Urnes, P. and Dozy, P., *Adv. Protein Chem.*, 16, 401 (1961).
Kyte, J. et al., *J. Mol. Biol.*, 157, 105–132 (1982).
Read, et al., *Proc. Natl. Acad. Sci. USA*, 75, 4514–4518 (1978).
Andrews, R. K. et al., *Biochemistry*, 28, 8317–8326 (1989).
Brinkhous, K. M. and Read, M. S., *Blood*, 55(3), 517–520 (1980).
Newman, et al., *Br. J. Hematol.*, 21, 1–20 (1971).
Marguerie, et al., *J. Biol. Chem.*, 254, 5357–5363 (1979).
Allain, et al., *J. Lab. Clin. Med.*, 85, 318–328 (1975).

*Primary Examiner*—Dian C. Jacobson
*Attorney, Agent, or Firm*—Synnestvedt & Lechner

[57] ABSTRACT

An aqueous solution of cysteine-altered von Willebrand Factor fragment which is substantially free of aggregate and capable of therapeutic use for treating thrombosis and a process for preparing such a solution comprising:

(A) providing an aqueous solution of the fragment and denaturant;

(B) purifying the solution of fragment and denaturant under conditions which promote conversion of aggregated forms of the fragment to the dimeric and/or monomeric forms thereof to provide purified fragment;

(C) separating the dissolved, purified fragment from the denaturant while maintaining the aqueous solution of the fragment at a pH of about 2.5 to less than about 5.5 to increase monomerization of, and decrease aggregation of, said purified fragment, thereby forming an aqueous solution of fragment which is substantially free of aggregate.

18 Claims, 4 Drawing Sheets

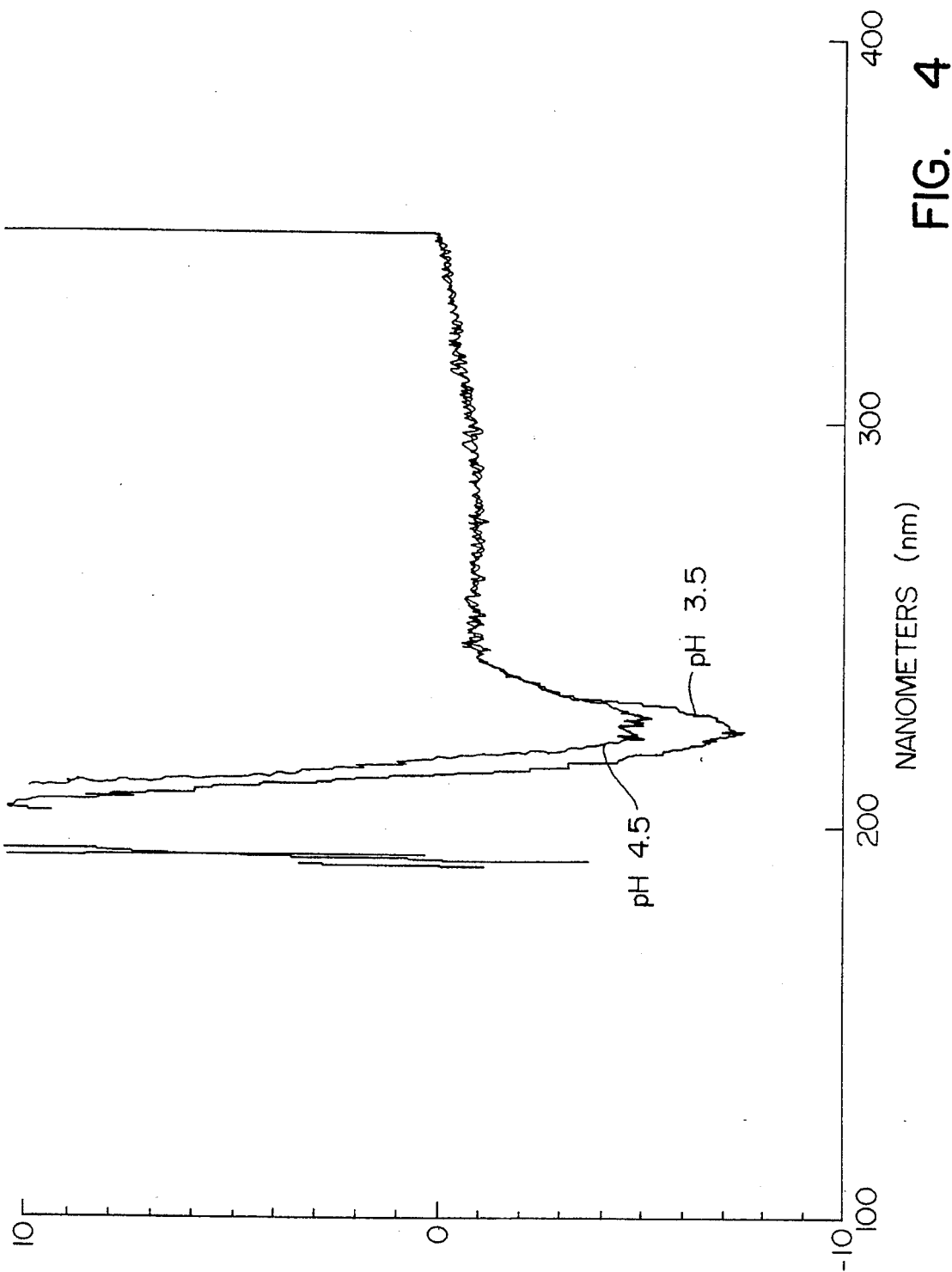

THERAPEUTIC FRAGMENTS OF VON WILLEBRAND FACTOR

This is a continuation of copending application Ser. No. 07/717,942 filed on Jun. 20, 1991 now abandoned.

FIELD OF THE INVENTION

This invention relates to therapeutic polypeptides. More specifically, this invention relates to purified fragments of von Willebrand factor that can be used, for example, in the treatment of vascular disorders such as thrombosis.

The term "hemostasis" refers to those processes which comprise the defense mechanisms of the body against loss of circulating blood caused by vascular injury. The present invention relates to the provision of therapeutically useful forms of polypeptides based on von Willebrand factor ("vWF"), one of the proteins of the hemostatic mechanism.

Processes which are normal as a physiologic response to vascular injury may lead in pathologic circumstances, such as in a patient afflicted with atherosclerotic vascular disease or chronic congestive heart failure, to the formation of undesired thrombi (clots) with resultant vascular occlusion. Impairment of blood flow to organs under such circumstances may lead to severe pathologic states, including myocardial infarction, a leading cause of mortality in developed countries.

The restriction or termination of the flow of blood within the circulatory system in response to a wound or as a result of a vascular disease state involves a complex series of reactions which can be divided into two processes, primary and secondary hemostasis. Primary hemostasis refers to the process of platelet plug or soft clot formation. Platelets are non-nucleated discoid structures approximately 2–5 microns in diameter derived from megakaryocytic cells. Effective primary hemostasis is accomplished by platelet adhesion, the interaction of platelets with the surface of damaged vascular endothelium on which are exposed underlying collagen fibers and/or other adhesive macromolecules such as proteoglycans and glycosaminoglycans to which platelets bind.

Secondary hemostasis involves the reinforcement or crosslinking of the soft platelet clot. This secondary process is initiated by proteins circulating in the plasma (coagulation factors) which are activated during primary hemostasis, either in response to a wound or a vascular disease state. The activation of these factors results ultimately in the production of a polymeric matrix of the protein fibrinogen (then called "fibrin") which reinforces the There are circumstances, however, where it is desired to prevent deposition of platelets in blood vessels, for example, in the prevention and treatment of thrombosis or stroke and to prevent occlusion of arterial grafts. Platelet thrombus formation during surgical procedures may also interfere with attempts to relieve preexisting vessel obstructions.

Antiplatelet drugs include compounds which suppress primary hemostasis by altering platelets or their interaction with other circulatory system components. A compound that has been disclosed for use as an antiplatelet drug is an alkylated fragment of vWF having a molecular weight of about 52,000 and derived by tryptic digestion of vWF and comprising approximately residues 449–728 thereof. This therapeutic fragment is the subject of European Patent Office Application Ser. No. 87304615, filed May 22, 1987, published under No. 25 5206 on Feb. 3, 1988. The disclosure of this publication is incorporated herein by reference.

By way of background, it is noted that vWF, on which the aforementioned fragment is based, is a high molecular weight multimeric protein which circulates in the blood and is involved in the clotting of blood. It is accepted that vWF causes platelets to bind to the damaged blood vessel by its forming a bridge between the platelets and the vessel. It is accepted also that platelet binding sites of vWF are contained within the aforementioned residues 449–728.

As to the functioning of the aforementioned alkylated vWF fragment as an antiplatelet drug, the fragment is believed to function by binding to the glycoprotein Ibα receptor of platelets thereby inhibiting binding to the platelets of the vWF in the blood. In effect, the vWF fragment occupies the surface receptor of GPIb that would normally be occupied by vWF of the blood, but because it lacks the bridging activity of the larger vWF molecule from which it is derived it does not initiate platelet adhesion or resultant clot formation.

In practice it is difficult to derive therapeutically useful quantities of this or other fragments of vWF from blood plasma. Difficulties include effective separation of the residue 449–728 fragment from other components, for example, tryptic digests, and requirements for effective sterilization of blood-derived components potentially contaminated with human viruses such as hepatitis and HIV. Accordingly, it has proved desirable to produce this fragment of vWF using recombinant DNA in host cells, including, for example, bacterial host cells.

vWF fragments produced by bacterial expression systems been unfortunately found to accumulate in large quantities as insoluble aggregates (inclusion bodies) within the host cells. For the purpose of deriving therapeutically useful formulations of the fragments (residues 449–728), it is necessary to extract the fragment in soluble form from the inclusion bodies contained in the host cells.

The present invention includes within its scope the recovery of a therapeutically useful fragment of vWF expressed from recombinant DNA molecules in host bacterial cells. The invention encompasses also the provision of such fragments in pure and unaggregated form, including therapeutic formulations which are substantially free of aggregate.

SUMMARY OF THE INVENTION

In accordance with the present invention, there is provided a process for preparing an aqueous solution of cysteine-altered von Willebrand factor (vWF) fragment which is substantially free of aggregate comprising:

(A) providing an aqueous solution of cysteine-altered vWF fragment and denaturant;

(B) purifying an aqueous solution of the fragment and denaturant under conditions which promote conversion of aggregated forms of the fragment to the dimeric and/or monomeric forms thereof to provide purified fragment;

(C) separating the dissolved, purified, fragment from the denaturant while maintaining the aqueous solution of the fragment at a pH of about 2.5 to less than about 5.5 to increase monomerization of, and decrease aggregation of, said fragment, thereby forming an aqueous solution of cysteine-altered vWF fragment which is substantially free of aggregate. In preferred form, the cysteine-altered vWF fragment of step (A) is provided as an alkylated fragment, the denaturant referred to in steps (A) and (B) is urea, and the pH is maintained at about 3 to about 4.

In addition to its role as a binding site for platelets, the residue 445–733 fragment of mature vWF subunit comprises a domain of the subunit which is responsible in vivo for noncovalent and covalent binding of vWF subunits to form large vWF multimers. Accordingly, there is a tendency for this polypeptide to dimerize and/or to form aggregates. This is undesirable because the most biologically active form of the fragment is the monomeric form. An aspect of the present invention, therefore, involves inhibiting formation of aggregates in formulations of cysteine-altered vWF fragment, such aggregates having little therapeutic utility in the treatment of cardiovascular disorders and potentially posing a risk of adverse clinical consequences.

Another aspect of the present invention relates to the provision of a process for limiting dimerization of monomeric cysteine-altered von Willebrand factor fragment, said dimerization involving one or more of ionic, hydrophobic or hydrogen bonds which facilitate in vivo the association of two or more mature vWF subunits, said process comprising forming an aqueous solution of monomeric cysteine-altered vWF fragment which has a pH of about 2.5 to less than about 5.5 and which includes therein up to about 10 mg/ml of said fragment and wherein the total concentration in the solution of additional species of ions (if any) is less than about 75 mM.

Still another aspect of the present invention is the provision of an aqueous formulation containing unaggregated cysteine-altered vWF fragment that can be stored effectively for considerable periods of time prior to administration to a patient. Accordingly, there is provided an aqueous formulation comprising unaggregated cysteine-altered vWF fragment which if lyophilized and then rehydrated, remains thereafter in substantially unaggregated form, that is, is substantially free of aggregate.

Yet another aspect of the present invention is the development of the capability to derive pure alkylated vWF fragment from inclusion bodies in a manner such that contaminating macromolecules, for example, host DNA and/or protein or endotoxin, are completely removed. Purification steps particularly useful for accomplishing this include: (A) separating the aforementioned type of contaminants from an aqueous solution of alkylated vWF fragment and denaturant by contacting a solution thereof having an alkaline pH with an anionic exchange material to which said contaminants adhere; (B) contacting the aqueous solution from which contaminants have been removed with a cationic exchange resin to which the alkylated vWF fragment adheres; and (C) eluting the alkylated vWF fragment from the cationic exchange resin by contacting the resin with an aqueous solution containing ionized citric acid and a nonionic denaturant wherein affinity of the eluted fragment for citrate ions of the mobile phase facilitates solubilization from the stationary phase.

Another aspect of the present invention provides a method of treating thrombosis in a patient using a therapeutic formulation of the invention.

BRIEF DESCRIPTION OF THE DRAWINGS

FIG. 4 shows the circular dichroism profile of unaggregated alkylated vWF fragment at pH 3.5 and pH 4.5.

DEFINITIONS

Figure 1:
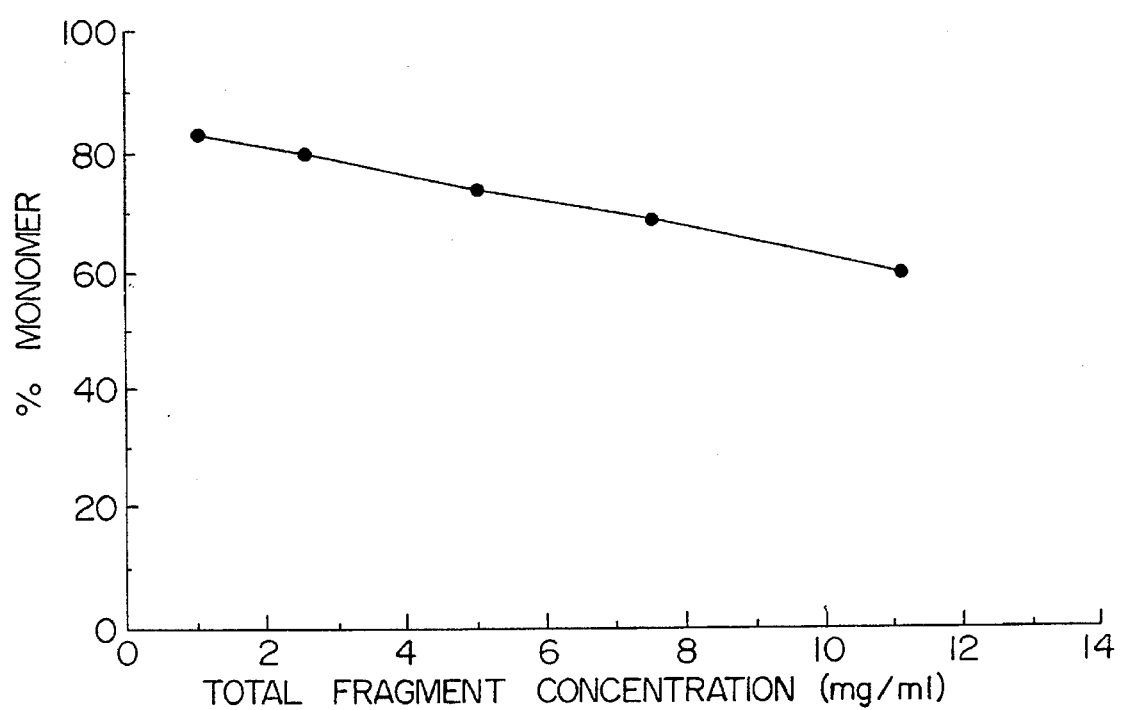
FIG. 1 is a profile of monomer/dimer equilibrium as affected by total concentration of alkylated von Willebrand factor fragment.

Unless indicated otherwise herein, the following terms have the indicated meanings.

cDNA

A DNA molecule or sequence which has been enzymatically synthesized from the sequence(s) present in an mRNA template.

Expression

The process undergone by a structural gene to produce a product. In the case of a protein product, it is a combination of transcription and translation.

Recombinant DNA Molecule

A molecule consisting of segments of DNA from different genomes which have been joined end-to-end and have, or can be modified to have, the capacity to infect some host cell and be maintained therein.

Cloning

The process of obtaining a population of organisms, or DNA sequences or other macromolecules derived from one such organism or sequence by asexual reproduction or DNA replication.

Biological Activity

One or more functions, effects of, activities performed or caused by-a molecule in a biological context (that is, in an organism or in an in vitro facsimile). A characteristic biological activity of the residue 445–733 monomeric fragment of the mature von Willebrand factor subunit is the potential ability to bind to the GPIbα receptors of platelets thereby inhibiting platelet agglutination.

An additional aspect of the characteristic biological activity of the residue 445–733 monomeric fragment of mature von Willebrand factor subunit is the ability to bind to only one platelet GPIbα receptor thereby enabling the molecule to inhibit botrocetin-induced binding of multimeric vWF to platelets. Other resultant or related effects of the monomeric 445–733 species include inhibition of platelet activation, or adhesion to surfaces. Thus, such a fragment has therapeutic utility as an antithrombotic agent.

Reducing Conditions

Refers to the presence of a "reducing" agent in a solution containing von Willebrand factor, or polypeptides derived therefrom, which agent causes the disruption of disulfide bonds of the vWF.

von Willebrand Factor (vWF)

It is understood that all references herein to von Willebrand factor refer to vWF in humans. The term "von-Willebrand factor" is intended to include within its scope the term "mature vWF" defined below.

Mature vWF

Circulating vWF as found in the plasma or as bound to the subendothelium. It consists of a population of polypeptide monomers which are typically associated into numerous species of multimers thereof, each subunit (monomer) of which being 2,050 residues in length. Additionally, when expressed in mammalian cells, mature vWF is usually glycosylated. von Willebrand factor is found as a component of the subendothelial matrix, as a component of the α-granules secreted by activated platelets, and as a circulating blood plasma protein.

Monomeric

When used with respect to cysteine-altered vWF fragment, "monomeric" refers to a single polypeptide which is neither covalently nor non-covalently linked to another polypeptide. "Dimeric" refers to a non-covalent association of two monomers. "Aggregated" cysteine-altered vWF fragment refers to structures larger than dimers.

Purified or Substantially in Pure Form

When used with respect to vWF-derived polypeptides, this and similar terms mean that the composition is substantially free of most of the cellular protoplasm, non vWF-protein, or extracellular material with which the polypeptide normally occurs in the body.

Table 1 shows the standard three letter designations for amino acids as used in the application.

TABLE I

| | |
|---|---|
| Alanine | Ala |
| Cysteine | Cys |
| Aspartic Acid | Asp |
| Glutamic Acid | Glu |
| Phenylalanine | Phe |
| Glycine | Gly |
| Histidine | His |
| Isoleucine | Ile |
| Lysine | Lys |
| Leucine | Leu |
| Methionine | Met |
| Asparagine | Asn |
| Proline | Pro |
| Glutamine | Gln |
| Arginine | Arg |
| Serine | Ser |
| Threonine | Thr |
| Valine | Val |
| Tryptophan | Trp |
| Tyrosine | Tyr |

DETAILED DESCRIPTION OF THE INVENTION

The antithrombotic polypeptide with which the present invention is concerned is a cysteine-altered vWF fragment which comprises the amino acid sequence domain of mature vWF subunit beginning with residue 445 (serine) thereof and ending with residue 733 (valine) thereof, and having an apparent molecular weight of approximately 33,000 in which cysteine residues thereof (positions 459, 462, 464, 471, 474, 509 and 695) are altered in a manner such that their tendency to interact with other cysteine residues is inhibited in a manner such that cysteine-based bonds are not capable of being formed within a single fragment or between fragments, the formation of such bonds tending to form materials which tend to be insoluble or biologically active. For convenience, such fragment is referred to herein as "cysteine-altered vWF fragment." This term includes within its scope fragments which encompass or overlap with the 445–733 residue sequence and contain all or part of the GPIbα binding domains thereof. The term "cysteine-altered vWF fragment" also includes polypeptides representing mutant amino acid sequences of the residue 445–733 domain which have antithrombotic utility. Such mutant sequences may or may not involve cysteine residues.

It is anticipated that forms of the polypeptide resultant from expression of an appropriate cDNA or other recombinant DNA molecule in a eucaryotic host cell can also be effectively monomerized and formulated according to the practice of the invention.

Inasmuch as the cysteine-altered vWF fragment is based upon a fragment of vWF, there is set forth hereafter information concerning this protein and its role in hemostasis and thrombosis. Von Willebrand factor exists in humans as a series of high molecular weight multimers of up to 30 glycosylated subunits per multimer in which the subunits are believed to be identical, with each having an approximate molecular weight of 270,000 (270 kDa). Each circulating "mature" human subunit consists of 2,050 amino acid residues.

Formation of an initial monolayer of platelets covering injured endothelial surfaces is believed to involve a bridging function in which surface bound multimeric vWF binds on the one side to components of the subendothelium, such as collagen or proteoglycans, and on the other side to the GPIb-IX receptor of a platelet membrane. It is believed that the interaction of multimeric vWF with glycoprotein Ib-IX complex (at GPIb(α)) results in platelet activation and facilitates the recruitment of additional platelets which function to form a growing thrombus. The rapidly accumulating platelets are also crosslinked by the binding of fibrinogen. Of particular importance in this process is the multimeric and multivalent character of circulating vWF, which enables the macromolecule to effectively carry out its binding and bridging functions.

The cysteine-altered vWF fragment to which the present invention relates in effect competes with vWF factor for GPIbα receptors and inactivates the receptors so they are not available for interaction with vWF, the result being that the formation of clots is inhibited. As to the nature of the fragment, prior research work has established that the domain of the 2,050 residue mature von Willebrand factor subunit which binds to the platelet membrane glycoprotein Ib-IX receptor (GPIb(α)) is the fragment thereof that extends from approximately residue 449 (valine) of the circulating subunit to approximately residue 728 (lysine) thereof. This fragment has an apparent molecular weight of approximately 52,000 and can be generated by trypsin digestion, followed by disulfide reduction of vWF. The GPIb(α) binding domain of vWF comprises residues contained in two discontinuous sequences $Cys^{474}$-$Pro^{488}$ and $Leu^{694}$-$Pro^{708}$ within the fragment. Mohri, H. et al., *J. Biol. Chem.*, 263(34), 17901–17904 (1988). Typically, the 52,000 molecular weight fragment is referred to as a "52/48" fragment reflecting the fact that human enzyme systems glycosylate the fragment contributing to its molecular weight. The amount of glycosylation varies from molecule to molecule, with two weights, 52,000 and 48,000, being most common. As expressed from recombinant bacterial host cells, the fragment lacks the posttranslational glycosylation associated with expression thereof in mammalian cells. Without the additional weight contributed by glycosylation, the polypeptide has a molecular weight of approximately 33,000. Both the "52/48" and "33" fragments competitively inhibit the binding of von Willebrand factor to platelets.

As mentioned above, it is difficult to derive therapeutically useful quantities of the vWF fragment from blood plasma. Accordingly, it has proved desireable to produce this fragment of vWF using recombinant DNA in host cells. A wide variety of recombinant systems are available for expression of a DNA sequence encoding the fragment. Examples of three systems are described-below. These systems have been used successfully and employ bacterial host cells and encode the slightly larger residue 445–733 fragment. The additional amino and carboxy terminal residue sequences have been determined to have no significant effect on the utility of the fragment as an antithrombotic.

(I) a vector designated pMMB3, incorporating a highly efficient $P_R$ promoter from bacteriophage lambda. Induction of vWF fragment expression in *E.coli* was achieved by growing the cells to mid-log phase at 30° C. and then shifting the temperature to 42° C.

(II) a vector designated pMMB5, incorporating a hybrid trp-lac (tac) promoter system regulated by the lac repressor. Induction in this system was achieved by growing cells to mid-log phase at 37° C. followed by the addition of the lactose analog IPTG.

Results obtained with pMMB3 and pMMB5 were very similar. Briefly, *E.coli* cells transformed with each of the above plasmids were. grown to mid-log phase, induced for 1–16 hours, harvested and fractionated into soluble and insoluble components. The vWF fragment exhibited extreme insolubility following lysis of either population of cells.

(III) A third vector (plasmid) used for expression of the vWF fragment, and conferring resistance to kanamycin ($Km^R$) contains a promoter from the bacteriophage T7. The vector was obtained from Dr. F. William Studier of Brookhaven National Laboratories and was constructed as follows. The plasmid was constructed by removing the ampicillin resistance gene from pET- 8c *via excision of a BspHI-EcoRI fragment (pBR322 bp 3195–4361)* and replacing it with an 869 bp fragment encoding kanamycin resistance ($Km^R$), with the $Km^R$ gene oriented clockwise in the vector. The $Km^R$ gene derives from Tn903 (Oka, et al., *J. Mol. Biol.*, 147:217–226 (1981)) and was obtained using the polymerase chain reaction with pUC4KISS Barany, F., Gene, 37:111–123 (1985)) as template. The fragment carrying the $Km^R$ gene starts 50 nucleotides ahead of the $Km^R$ initiation codon and ends exactly at the termination codon.

A plasmid expressing the vWF fragment and conferring resistance to kanamycin was constructed from a vector designated pET-8c52K and pET-8c($Km^R$). Briefly, an XbaI/BamI fragment encoding the vWF fragment was excised from pET-8c52K and ligated into XbaI/BamHI cleaved pET-Sc($Km^R$). The resulting plasmid DNA (pET-8c52K9$Km^R$)) was transformed into *E.coli* DH-1 cells and a single isolate was identified that released the appropriate size fragment by digestion with Xba/BamHI. DNA from this isolate was then Used to transform *E.coli* BL21(DE3)pLysS. A single isolate from this transformation was then used for expression of vWF fragment.

In this system, the vWF DNA is placed into a vector- containing the promoter and translation initiation signals for the Tφ protein of bacteriophage T7. T7 RNA polymerase can then be delivered to the host cell by either induction or infection. In this particular case, the vWF expression vector was placed into a cell that carries a prophage containing the gene for T7 RNA polymerase under control of the lac UV5 promoter. Addition of the lactose analog IPTG to a growing culture of cells induced T7 RNA polymerase, which in turn transcribed the target DNA in the plasmid. Transcription by T7 RNA polymerase was so active that target RNA accumulates to amounts comparable to ribosomal RNA and target protein constitutes a major fraction of cellular protein. As an initial characterization of the synthesis of vWF fragment, cells were induced and samples taken at time points between 0.5 and 16 hours post induction. These data indicated that by 4 hours post induction, vWF fragment constituted approximately 25% of total cellular protein. This level is much higher than that generated either by the tac or the $P_R$ vector system.

Of particular significance to the provision of therapeutic polypeptides from recombinant systems is the ability to cause expression of pharmacologically useful quantities of the therapeutic. Of the three systems referred to above, system (III) is preferred because it produces a greater yield of fragment.

vWF fragments produced by a bacterial expression system such as, for example, system (III) tend unfortunately to accumulate in large quantities as insoluble aggregates (inclusion bodies) within the host cells, there being no mechanism available in the host cells to trigger their effective secretion therefrom. For example, a mammalian signal peptide would not generally be recognized in the bacterial system. Such insoluble aggregates of expressed polypeptide (inclusion bodies) are a well known result of attempting to produce large quantities of useful protein from recombinant bacterial systems, Williams, D. C. et al., *Science*, 215, 687–689, (1982), and may reflect improperly folded polypeptides.

It is theorized that formation of the inclusion bodies is related to the presence therein of a high effective concentration of cysteine residues. It is believed that incorrect disulfide bonds are encouraged to, and do, form either within the inclusion bodies or during attempts to solubilize the polypeptides therefrom. When formed within a fragment (an intrachain bond), such bonds may lead to a biologically inactive conformation of the molecule. When formed between fragments (an interchain bond) such bonds may lead to insoluble or biologically inactive dimers or aggregates. The vWF fragment comprising residues 445–733 contains seven cysteine residues at positions 459, 462, 464, 471, 474, 509 and 695. Thus, successful manipulation of mammalian proteins expressed from recombinant bacterial systems has generally required that the cysteine residues thereof be altered so that they cannot react with other cysteine residues. Without this treatment, undesired reaction of the cysteine residues thereof typically occurs, leading to the formation of insoluble or biologically inactive polypeptide aggregates unsuited for effective use as therapeutics.

There are available numerous well known procedures which can be used to successfully alter cysteine residues. One such technique involves treatment of cysteine residues with a reducing agent. Such as, for example, β-mercaptoethanol or dithiothreitol "DTT" followed by permanent alkylation (for example, with iodoacetamide) of the seven cysteine residues of the fragment. Numerous other covalent labels may be attached to the target cysteine residues, the only requirements being that the label can be applied under pH conditions which do not irreversibly denature the target protein, said attachment being of a kind which under the conditions to which the fragment is exposed during further processing or storage, will not allow chemical reaction with other cysteine residues. Such covalent labelling procedures are generally known in the art and include also, for example, reaction with (A) iodoacetic acid or (B) iodinating agents such as iodofluorescein. Additionally, cysteine residues may be chemically altered such as by sulfitolyzation. Alteration can be accomplished also by site directed mutagenesis of an encoding DNA, replacing cysteine residues with "inert" residues such as, for example, glycine or alanine, or by deletion of sequence positions corresponding to cysteine. A sufficient number of the cysteine residues are altered to avoid the problems caused by their presence.

As described in Example 1 below, it is preferred that the aggregation effects caused by incorrect disulfide bonding be eliminated with respect to the therapeutic formulations of this invention by chemical reduction (with dithiothreitol, "DTT") followed by permanent alkylation (with iodoacetamide). In spite of this treatment, the resulting polypeptide (hereinafter designated the "alkylated vWF fragment" of the invention) has been found to remain accumulated in aggregated, and therefore therapeutically-useless, form. Other types of cysteine-altered fragments can be equally resistant to solubilization for therapeutic formulation, the aggregation behavior responsible therefor being unrelated to the cysteines.

Accordingly, this invention provides treating steps which are effective in solubilizing the aggregated cysteine-altered fragment and it provides aqueous solutions of the fragment which are acceptable, for example, for injection into patients, such solutions containing the dissolved fragment being in unaggregated and therapeutically useful form.

Thus, the present invention includes within its scope an identification of conditions under which the expressed vWF fragment, comprising inclusion bodies, can be provided first as unaggregated cysteine-altered fragment stabilized in a solution containing denaturant and second, as unaggregated fragment stabilized in a solution containing only therapeutically acceptable substances compatible with injection into humans.

Any suitable means can be utilized to recover the vWF fragment from the recombinant system in which the fragment is prepared. As an initial step, the insoluble aggregates of fragment, that is, the inclusion bodies, are separated from other cellular components. This involves disruption of the host cells and separation of the ruptured cell materials from the insolubilized protein (as inclusion bodies). Examples of available means for accomplishing this are procedures involving the use of sonication and homogenation. Representative procedures include those described in U.S. Pat. Nos. 4,828,929 and 4,673,641.

A preferred procedure for extracting the inclusion bodies from host cells is described in Example 1 below and involves repeated cycles of the use of mechanical homogenation for effecting cell-disruption in the-presence of one or more detergents and separation of the ruptured cell materials from the vWF fragments by centrifugation. It should be understood that other available procedures can be used also.

The aggregated vWF fragment recovered from the recombinant system comprises a broad spectrum of polypeptides ranging from soluble trimers of the fragment to macroscopic insoluble structures in which thousands of such individual polypeptide fragments are bound. Typically, however, those aggregates composed of approximately 10 to 20, or fewer fragments, and having a molecular weight of 200,000 to 400,000 are soluble. Such fragments, which are referred to herein as "soluble aggregate", have relatively low therapeutic utility as measured in in vitro assays (see Example 3 and FIG. 3). Certain even larger complexes are also soluble, although also of relatively low therapeutic utility.

The "unaggregated fragments" (or fragments "substantially free of aggregate") which result from the process described herein comprise a population composed of monomeric fragment and also of noncovalently linked dimeric fragment. Based on experiments using high performance liquid chromatography (HPLC), the amount of."soluble aggregate" present in such samples is less than about 0.5%. In fact, it is expected for most preparations that the % contamination is lower, being in large measure an artifact of the salt environment of the HPLC system. As will be discussed below, dimers so isolated exist in equilibrium (FIG. 1) with the monomer and have been determined to have on average one-half the anti-platelet agglutination activity of monomers, on a per weight basis. This suggests the masking of one of two binding sites within the dimer. In connection with the production of therapeutically useful samples of unaggregated fragment, the preparation of samples which contain a major amount of monomer and a minor amount of dimer is preferred.

In the practice of the invention, the process for preparation of solubilized and unaggregated fragment begins with a step that converts insoluble aggregate into soluble aggregate. This involves the preparation of an aqueous solution containing the cysteine-altered vWF fragment and denaturant.

The preferred form of the invention involves permanent alkylation of the fragment in an aqueous solution under conditions in which a denaturant facilitates formation of soluble aggregates of fragment. Dissociation of the aggregated material can bemonitored by any of several well known techniques including gel chromatography based on size exclusion and ultracentifugation.

Alkylation of the fragment is preceded by reduction of the intra and interchain disulfide bonds in the inclusion body aggregate. This is followed by permanent alkylation of reduced cysteine residues. Both reduction and alkylation of the fragment can be effected by any suitable means, such treating steps for proteins being known.

Reduction generally involves reacting an aqueous solution of the aggregate with a suitable reducing agent under conditions which convert the disulfide bonds of the protenacious aggregate to thiol groups. Examples of reducing agents that can be used are β-mercaptoethenol, and dithiothreitol, the last mentioned being preferred.

The product of reduction can then be subjected to alkylation under conditions such that the alkylating agent functions to permanently and covalently label the free sulfhydryl groups of the fragment in a manner such that they are and remain inactive as the protenacious fragment is subjected to further manipulation or storage. Any suitable alkylating agent can be used. Examples of such agents include iodoacetic acid, and iodoacetamide, the last mentioned being preferred.

In accordance with the invention, the cysteine-altered vWF fragment, including the alkylated form thereof, and subsequent production of unaggregated fragment is effected by manipulating the fragment in an aqueous solution containing denaturant. The term "denaturant", as used herein, refers to substances which at appropriate concentrations are capable of changing the conformation of fragments, typically by one or more of the following representative mechanisms: altering the solvent environment, that is, the state of hydration of certain groups of the fragment, by providing certain solvent surface interactions or by disrupting ionic or hydrogen bond contacts or other interactions within or between fragments. Generally, the effects of a denaturant are reversible. For example, upon dialysis against a solution containing no denaturant, the effect induced by the denaturant is reversed. The nature of the denaturant used in the practice of the present invention and conditions of treatment are such that the effects of the use of the denaturant are reversible. Accordingly, the use of materials or conditions which cause an irreversible effect should be avoided, for example, the use of high temperature or the application of substances which bind to the fragment with such high affinity as to be, in a practical sense, impossible to remove.

The terms "denaturant" and "detergent" as used herein, are deemed to be equivalent as long as the above criteria are satisfied. Examples of suitable materials for use as denaturants in the present invention include urea and guanidinehydrochloride, and detergents such as, for example, polyoxyethylene (9) p-tert-octylphenol (Nonidet® P40), polyoxyethylene (9-10) p-tert-octylphenol (Triton-X-100), and sodium deoxycholate.

The most preferred denaturant for use in the present invention is urea. It is highly soluble in aqueous solutions and it is capable of being removed rapidly from solution by dialysis. Because urea is a nonionic substance, it does not interfere with ion exchange materials that may be used in the process to remove contaminants of bacterial origin such as DNA and endotoxin, as described below. A recommended concentration range of urea is about 4 M to about 8 M.

Practice of the present invention can include also steps which have been found particularly useful to remove from the cysteine-altered vWF fragment contaminants of bacterial origin such as, for example, bacterial DNA, bacterial endotoxin (lipopolysaccharide) and bacterial proteins. The removal of such contaminants permits the fragment to be used in therapeutic formulations. Stated generally, the process involves subjecting an aqueous solution of the impure alkylated vWF fragment and denaturant to an anion exchange material and then to a cation exchange material.

Treatment of the contaminant-containing solution with the anion exchange material is effected at alkaline pH and is effective in removing from the solution bacterial DNA and endotoxin which adhere to the anion exchange material. For this purpose, the solution should contain a quantity of salt in an amount such that the bacterial components adhere to the anion exchange material and the vWF fragments do not.

The solution is then contacted at acidic pH with a cation exchange material to which the fragment binds, thus separating the fragment from bacterial protein. The acidic pH of the solution should be such that some of the carboxyl groups of the cation exchange material are ionized and some of the carboxyl groups on the fragment are protonated to avoid aggregation. Elution of the fragment from the cation exchange material can be effected with a suitable elution buffer, for example, and preferably, an aqueous solution containing ionized citric acid and a nonionic denaturant.

Example 1 below describes a preferred series of steps which are representative of methods that effectively separate from the fragment bacterial contaminants under conditions in which the overall goal of the process—converting the population of cysteine-altered vWF fragments into unaggregated fragments—is achieved.

Although guanidine hydrochloride is considered a preferred denaturant, it interferes with ion exchange materials and must be substantially removed prior to any ion exchange steps that remove contaminants of the aforementioned type.

A recommended concentration of guanidine hydrochloride is about 4 to about 8 M.

It is important that the fragment be maintained during further solubilization in the presence of denaturant at a pH of about 2.5 to below about 5.5. Titration of the amino acid side chains of alkylated vWF fragment with acid demonstrates that the fragment becomes fully protonated at pH 3.5, the polypeptide fragment bearing then a net charge of (+)41. It is believed that maintenance of the fragment in an environment which maximizes net charge is important to maintaining the solubility of the fragment, facilitating dissociation of soluble aggregates to smaller aggregates and to unaggregated material, and also preventing reassociation of fragments. A pH value of about 3 to about 4 is preferred. Solubilization in the presence of denaturant at pH 3.5 is most preferred. Any suitable acid can be used to adjust the pH. Examples of acids which can be used include hydrochloric acid or lactic acid. However use of an acid providing buffering capacity in the pH range of about 3 to about 5 is preferred. The use of citric acid is most preferred.

Although numerous procedures are known for solubilizing aggregated inclusion body proteins in the presence of denaturant, any clinical use of the resultant product requires that the denaturant contained therein be replaced with clinically acceptable materials which are nontoxic and nonirritating, so that the resultant solution complies with legal standards for injection into humans. Attempts to formulate cysteine-altered vWF fragment, and even fragment in alkylated form reconstituted from inclusion bodies, in a solution having a physiological pH or a concentration of ions reflective of the salinity of blood have produced only products which contain insoluble aggregated protein.

Thus although monomerizing the cysteine-altered fragment with denaturants produces a composition in which the fragments have been substantially dissociated, successful formulation of the polypeptide for clinical use without denaturant has proved heretofor impossible. Although a net charge of +41 is obtained on the vWF fragment at pH 3.5 and although such charge is representative of or even more substantial than the net charge which can be generated on many proteins of comparable size, monomeric molecules so produced reaggregate in the absence of denaturant. There follows hereafter a discussion of process steps which enable one to prepare a clinical formulation of a soluble form of the cysteine-altered vWF fragment and to store and dispense it.

An important aspect of the present invention is the recognition that the solubility of cysteine-altered vWF fragment in a solution of acidic pH is enhanced if the solution contains a relatively low concentration of ionic substances. Such substances may take the form of organic or inorganic salts, buffers, amino acids or other charged molecules. As elaborated below, it is believed that maintaining the cysteine-altered fragment in such an aqueous solution facilitates, relative to solutions having physiological values of pH and ionic salt concentration, the solubilization of semipolar or hydrophobic groups of the fragment by the aqueous solution. Accordingly such solutions are used to replace denaturant-containing solutions described above for the storage of clinical formulations.

In the practice of the invention, the concentration of ionic substances, defined as the sum total of concentration of the positive and of the negative ions which are additional to the contribution of charged groups provided by the fragment, should not exceed about 75 mM in an aqueous solution of the fragment. When this concentration is exceeded, absent the presence of denaturant, aggregation of the cysteine-altered vWF fragments is of such significant magnitude that the material is unsuited for long-term storage for clinical use whether in solution or when thawed from frozen storage or when reconstituted from lyophilized form, and as elaborated below, may be further unsuited for temporary storage prior to further processing.

The concentration at which cysteine-altered vWF fragment, substantially free of aggregate, is present in the aqueous formulations of the invention can vary over a relatively wide range, for example, about 1 to about 30 mg/ml. Thus, cysteine-altered fragment can be made soluble, for example, in the preferred formulations, at up to at least about 30 mg/ml without formation of soluble aggregate. Because of the equilibrium that exists between monomers and dimers of the "unaggregated" cysteine-altered fragment, and because of the higher specific inhibitory activity of the monomer (see Example 2, and FIG. 1), concentration ranges that favor monomer such as up to about 15 mg/ml are preferred, with about 5 to about 10 mg/ml, a concentration particularly suitable for effective dosing, being most preferred.

Preferred in the practice of the invention is a therapeutic formulation containing up to about 10 mM of inorganic salt, up to about 15 mM of an additional ionic compound, such as, for example, an amino acid hydrochloride, and up to about 10 mM of a buffer. With respect to discussion of preferred concentration ranges of the above or similar compounds, it is understood that "mM" refers to the concentration of compound, not of the individual ions whose sum total should not exceed about 75 mM.

Additionally, a nonionic tonicity modifier, such as a sugar or sugar derivative, including, for example, mannitol, sucrose, or maltose may be added to the formulations of the present invention, either prior to storage in liquid form or prior to the lyophilization thereof. The amount thereof can comprise about 0 to about 15% (w/v). Such preparations may be frozen and then thawed for therapeutic use.

A preferred aqueous formulation comprises NaCl or other inorganic salt at about 0.5 to about 10 mM, citric acid or other appropriate buffer at about 0.5 to about 5 mM, and lysine monohydrochloride or other amino acid at about 0.5 to about 15 mM.

A highly preferred embodiment of the present invention is a solution having a pH of about 3.5 and comprising about 1.5 mM of NaCl, about 1 mM citric acid, and about 1 mM of lysine monohydrochloride. Addition of a nonionic tonicity modifier such as, for example, mannitol at about 5% (w/v) makes the formulations of the invention isotonic approximately with physiological solutions.

Following the processing steps described herein, it is possible to prepare an aqueous solution of cysteine-altered vWF fragment which is substantially free of aggregate. The term "substantially free of aggregate" includes a therapeutic solution or other pharmaceutical composition of cysteine-altered vWF fragment which contains an amount of soluble aggregate and/or of insoluble aggregate which is insufficient to trigger adverse clinical consequences in patients when administered in therapeutic doses.

The practice of the present invention can be utilized to prepare aqueous solutions of cysteine-altered fragments, substantially free of aggregate wherein the concentration of fragment therein is from about 1 to about 30 mg/ml, preferably from about 5 to about 15 mg/ml and most preferably about 10 mg/ml.

The practice of the invention can also be utilized to prepare aqueous solutions of cysteine-altered fragments substantially free of aggregate wherein the percent by weight of monomer is at least about 40 to about 100%, preferably at least about 65 to about 80 weight % and most preferably at least about 75 weight %.

Cysteine-altered vWF fragment may be formulated for storage in unaggregated form in pyrogen-free deionized water, the resultant pH being adjusted to about 3.5, without additional buffers, salts, or ionic compounds except as necessary to so titrate the preparation. In such a case, addition of a nonionic tonicity modifier is preferred. Such preparations may also be lyophilized or frozen and then thawed for therapeutic use. Thus, the invention provides therapeutic solutions having such stability that they may be lyophilized or frozen, and then reconstituted or thawed, such that upon such treatment the original activity returns.

Compositions produced according to the practice of the invention can be stored for at least one month at 4° C., the composition remaining substantially free of aggregate.

With respect to the selection of a preferred pH for storing a solution, or for such solution prior to lyophilization or freezing thereof, it is noted that titration with acid of the amino acid side chains of the cysteine-altered fragment, thereby generating the full (+)41 charge fragment, is complete at approximately pH 3.5. Accordingly, formulations in the range of pH of about 3 to about 5 are preferred. Greater acidity may denature the protein, whereas higher pH values approach too closely the isoelectric pH (5.5) of the protein, at which aggregation would occur.

It is noted also that formulations having a pH outside of the preferred range or containing a concentration of ions outside of the preferred range may be nonetheless suited for storage of an aqueous solution of alkylated fragment for intermediate periods of time (such as prior to additional processing) prior to long-term storage.

Cysteine-altered vWF fragment provided from vWF as isolated from the circulatory system or from a recombinant mammalian system can also be formulated according to the practice of the invention with enhanced solubility and stability characteristics. The formulation so prepared may be isotonic with the blood, or may be hypertonic or hypotonic thereto.

It is believed that the monomerization and formulation procedures of this invention are effective, at least in part, because treatment conditions disclosed herein enable advantage to be taken of the properties of certain hydrophobic and hydrophilic amino acid residues and resultant domains within the sequence of cysteine-altered vWF fragment. It has been previously mentioned that maintenance of the cysteine-altered fragment at pH 3.5 confers upon the polypeptide a net charge of +41 which is believed to enhance its hydrophilic character and hence solubility. Titration (protonation) of glutamic and aspartic acid side chains at or below about pH 4.5 is a potentially significant modulator of protein structure which may also explain the stabilization against aggregation conferred on the vWF fragment by storage at pH 3.5.

It is well known that charged side chains of amino acid homopolymers can destabilize e-helixes. Uncharged poly-L-glutamic acid and poly-L-lysine, for example, form stable α-helical structures whereas the charged forms thereof are stable only as random coil regions. Urnes, P. and Dozy, P., *Adv. Protein Chem.*, 16, 401 (1961), Lehninger, A. L., *Biochemistry*, p.113, Worth Publishing Company (1970). It is expected that appropriately positioned glutamic and aspartic acid residues, when negatively charged will also destabilize α-helical regions within the cysteine-altered vWF fragment. In protonated form, however, for example at pH 3.5, they are more likely to accomodate being included in or allowing vicinal formation of, or propagation of, ordered structural regions.

It is believed that to the extent that such ordered structural regions are enlarged, or formed by asparate or glutamate protonation at pH 3.5, they will restrict the facility with which any such regions (formerly present as a random coil containing hydrophobic residues at approximately pH 7.0) may bond. It is anticipated that such effects may be measured by an increase in the activation enthalpy needed for hydrophobic association.

It is also expected that such associations are minimized in aqueous solutions which, compared to physiological solutions, contain a substantially lower concentration of dissolved ionic substances.

It is expected that whether maintenance at pH 3.5 will or will not facilitate monomerization of, and inhibit aggregation of, a particular protein is dependent on the total number of aspartate and glutamate residues in the polypeptide structure and on their spacing with respect to subdomains of particular amino acid residues whose potential to participate in ordered structure is dependent in part on the protonation status of proximal glutamate and aspartate. It is evident therefore that whether placement at pH 3.5 of cysteine-altered recombinantly produced polypeptides will facilitate or stabilize monomerization thereof, is a question which must be addressed on a polypeptide species by species basis.

Particular factors useful in evaluation of the potential utility of low pH formulation to avoid aggregation behavior otherwise apparent under storage conditions at physiological pH 7.0 are hereinafter presented using cysteine-altered vWF fragment as a model.

(A) the cysteine-altered residue 445–733 vWF fragment contains 21 glutamate-and 15 aspartate residues out of a total of 289 sequence positions indicating that a significant number of sites in which ordered secondary structure is disturbed at pH 7.0 may become ordered on protonation of particular glutamic acid or aspartic acid residues;

(B) many classically hydrophobic residues are known to prefer or allow $\alpha$-helical or $\beta$-pleated sheet domains and may, because of sequestration in an ordered structural subdomain at pH 3.5, be less able to participate in hydrophobic aggregation. Such residues include alanine, leucine, phenylalanine, tyrosine, tryptophan, cysteine, methionine, asparagine, glutamine and valine. Whether a particular subregion adjacent to an Asp or Glu residue is of a hydrophobic nature such that it would be useful to confer upon it ordered secondary structure as may be allowed by glutamate or aspartate protonation may be answered in part by reference to the model of Kyte, J. et al., *J. Mol. Biol.*, 157, 105–132 (1982). The Kyte model predicts the extent of hydrophobic (or hydrophilic) character which a particular peptide sequence will exhibit when present in larger polypeptides. An overall hydrophobicity/hydrophilicity index is assigned based on individual residue contributions and the position of particular amino acids in relation to each other in the target sequence.

(C) There are within the residue 445–733 fragment numerous sequences of 5 or more residues where it is expected that ordered structure may be enhanced by protonation of glutamic or aspartic acid in the pH 3.5 to 4.0 region, relative to the order achieved at near pH 7.0. Representative domains whose $\alpha$-helical character may be enhanced at pH 3.5 include the following (with reference to the published sequence):

(1) $Cys^{464}$- $Leu^{469}$ (containing Asp at 465);
(2) $Cys^{471}$- $Glu^{476}$ (containing also Glu at 472);
(3) $Leu^{494}$- $Ile^{499}$ (containing Glu and Asp at 497, 498 respectively);
(4) $Leu^{512}$- $Asp^{520}$ (containing also Asp at 514);
(5) $Glu^{527}$- $Leu^{533}$ (containing also Glu at 529, 531);
(6) $Val^{537}$- $Glu^{542}$ (containing also Asp at 539);
(7) $Val^{533}$- $Tyr^{558}$ (containing Glu at 557);
(8) $Val^{680}$-$Gln^{686}$ (containing Asp at 681 and Glu at 682, 684); and
(10) $Tyr^{693}$ - $Ala^{698}$ (containing Asp at 696).

The increase in ordered structure which may be produced in unaggregated cysteine-altered vWF fragment by a pH shift from 4.5 to 3.5 is described in Example 4 and FIG. 4 thereof.

With respect to therapeutic use of formulations of cysteine-altered vWF fragment which are substantially free of aggregate, the amount to administer for the prevention or inhibition of thrombosis will depend on the severity with which the patient is subject to thrombosis, but can be determined readily for any particular patient. The formulations of the present invention comprising solutions, or lyophilized material resuspended, may be directly injected into patients or mixed with other physiologically compatible substances, such as nonionic tonicity modifiers just prior to injection.

EXAMPLES

Example 1

Preparation of Alkylated von Willebrand Factor Fragment in Unaggregated Form

The following procedure is designed to (1) place in solution soluble aggregates (typically 200 kDa or higher) dissolved from an inclusion body pellet of vWF fragment, as referred to below; (2) remove contaminants which are unacceptable in therapeutic formulations (such as bacterial DNA and endotoxins); (3) initiate "monomerization" of the fragment in a series of steps that result in smaller and smaller aggregates; and (4) provide the resultant unaggregated material in a formulation buffer which stabilizes the fragment against reaggregation.

Inclusion body pellet material was obtained from an appropriate culture of *E.coli* BL21(DE3)pLysS as follows. Cells were harvested from 50 liters of aerated culture and concentrated using hollow fiber microfilter membrane cartridges. Two Amicon H5MPO1-43 filter cartridges were employed in a recirculating mode. Cells were concentrated to a volume of 2 to 4 liters on the Amicon filters, after which the cells were washed by diafiltration in the Amicon filtration apparatus with 5 volumes, approximately 10 to 20 liters, of Tris buffered saline (0.025 M Tris, 3.03 gms/liter $H_2O$, 0.2 M NaCl, 11.7 gms/liter $H_2O$, Final pH 7.5±0.2, 25° C.; referred to hereinafter as A-1).

Cells were recovered from filtration in 4 liters of Tris buffered saline (A-1). In preparation for disrupting the cells, sodium deoxycholate was added to the cell suspension to reach a final concentration of 0.5 g/liter. The cells were mechanically disrupted by passage through a Microfluidizer® (Microfluidics Corp., M-110Y Microfluidizer®) immediately after collection. After the cells had passed once through the Microfluidizer®, a second detergent, Tween 80 was added to the suspension of lysed cells to reach a final concentration of 0.025%, using 25 ml of 2.5% Tween 80 (v/v), dissolved in 1 liter of TBS. This is performed by warming Buffer A-1 and adding the Tween 80, dropwise into the solution and mixing until the solution is visibly homogeneous. The solution was cooled to room temperature and then added to the disrupted cell suspension to yield a final concentration of 0.025% (v/v); (hereinafter A-2). If the Tween is present in the first passage, the Microfluidizer® can become obstructed and will require clearing the flow-path before cells can be disrupted. After the cells have been disrupted, the suspension was centrifuged (10,000×g; 35 minutes, 4° C.) to separate the inclusion bodies, which are primarily product, from the soluble cell debris. At this stage, the inclusion bodies may be stored overnight at −20° C.

The inclusion bodies were resuspended in 35 ml of Tris buffer A-3 per gram of inclusion body wet weight, determined by difference in weight of the centrifuge tube (A-3 - 0.05 M Tris, 6.06 gms/liter $H_2O$, 1.21 mM sodium deoxycholate, 0.5 gms/liter $H_2O$, 2 mM dithiothreitol (DTT), 0.31 gms/liter $H_2O$, 2 mM EDTA, 0.74 gms/liter $H_2O$, 5% (v/v) glycerol, 50 ml/liter $H_2O$, 0.025% (v/v) Tween 80, 10 ml 2.5% Tween 80 (A-2)/liter $H_2O$, Final pH 9.0±0.2, 25° C.). The inclusion body pellets were routinely resuspended in buffer by using a Polytron homogenizer (Brinkmann). The resuspended inclusion bodies were passed through the Microfluidizer® to assure thorough mixing with the buffer. After passage through the Microfluidizer®, the inclusion bodies were collected by centrifugation. The wash procedure was carried out a total of three times with Tris buffer A-3. At the end of the third wash, the pelleted inclusion bodies are resuspended in Tris buffer A-4, which does not contain the detergents deoxycholate or Tween (A-4 - 0.05 M Tris, 6.06 gms/liter $H_2O$, 2 mM dithiothreitol (DTT), 0.31 gms/liter $H_2O$, 2 mM EDTA, 0.74 gms/liter $H_2O$, 5% (v/v) glycerol, 50 ml/liter $H_2O$, Final pH 9.0±0.2, 25° C.). The fourth and last wash was carried out with Tris buffer A-4. The crude product was collected after centrifugation, drained dry, and may be stored at −70° C.

Each gram of inclusion body pellet was dissolved in 7.5 ml volume of buffer comprising 6 M urea, 0.05 M Tris·HCl, and 1 M sodium chloride, pH 8.8. The resultant "solubilized" vWF material represents a heterogeneous population of soluble aggregates having typically a molecular weight of approximately 200 kDa or higher.

The mixture was placed under a nitrogen atmosphere and dithiothreitol (DTT) was added to a final concentration of 0.01 M, with gentle stirring, to reduce the disulfide bonds of the fragment. Stirring of the mixture was continued in darkness for 1 hour at 37° C. Iodoacetimide (Sigma Chemical Co., St. Louis, Mo.) was added to a final concentration of 0.05 M. Incubation in the dark was continued for one hour at 37° C. Additional DTT was then added to raise the final concentration of DTT to 0.03 M. The solution containing alkylated vWF fragment was then passed through a 0.2 micron filter and transferred to a cold room maintained at 4° C.±2° C. Subsequent purification procedures were performed in a cold room, at 4° C., using reagents preequilibrated at that temperature.

The alkylated material was diluted 5 fold by addition of a buffer comprising 6 M urea, 0.05 M Tris·HCl, 5 mM disodium EDTA, at pH 8.0. The resultant solution contains also 0.2 M of NaCl carried forward from the alkylation solution. The diluted vWF preparation was chromatographed on a 252 mm×150 mm column of 45–165 micron bead-formed agarose particles having quatenary ammonium side chains suitable for anion exchange (Q-Sepharose®, Pharmacia, Uppsala, Sweden) which had been preequilibrated with buffer comprising 6 M urea, 25 mM Tris·HCl, 0.02 M potassium chloride, 0.1 mM disodium EDTA, 0.1 mM DTT, pH 8.0. Under these conditions, the von Willebrand factor fragment did not bind to the Q-Sepharose®; however contaminants such as negatively charged DNA and bacterial endotoxin, including lipopolysaccharide, were bound.

The net charge on each monomeric unit of polypeptide within the soluble aggregates is approximately (−2) under these conditions. It is believed that this low net charge in combination with the high salt concentration of the applied sample prevents aggregate binding to the stationary phase. The unbound fraction-containing vWF fragment, primarily as a population of soluble aggregates, was then filtered through a 0.2 micron filter, after which the filtrate was diluted 10 fold by addition of a buffer comprising 6 M urea, 0.01 M sodium citrate, pH 3.5. The resultant preparation was then held approximately 1 hour at 4° C. During this period, dissociation of the soluble aggregates commenced, shifting the fragment population to smaller aggregates and to monomeric and dimeric molecules.

The pH of the preparation was then adjusted to 4.8 by the addition of a sufficient volume of unbuffered 1.0 M sodium citrate, after which the preparation was passed over a bead-formed agarose gel formed of 45–165 micron particles containing carboxymethyl side chains capable of cation exchange (CM-Sepharose®, Pharmacia, Uppsala, Sweden) preequilibrated in buffer comprising 6 M urea, 0.01 M sodium citrate, pH 4.8, the pH being selected as a compromise between the need to maintain the resin carboxyl groups in unprotonated form, and to avoid shifting the fragment population back to the aggregated state by approaching too closely the isoelectric pH of the fragment (approximately 5.5). A pH of 3.0 would have been otherwise preferable to drive the fragment population toward dimers and monomers.

When loaded in this fashion, approximately 80–100% of the product vWF fragment fragment bound to the CM-Sepharose®. The column was then washed with a pH 4.8 buffer containing 6 M urea and 0.01 M sodium citrate until no further UV absorbing material (measured at 280 nm) was detected in the effluent. The elution buffer was then changed to 6 M urea, 0.01 M sodium citrate, 0.15 M sodium chloride, pH 4.8. A small amount of additional UV absorbing material was detected eluting from the column in this solution. Substantial amounts of remaining bacterial endotoxin were removed in this way. Elution was continued until no such further UV absorbing material was detected. The CM-Sepharose-bound fraction was then washed with a buffer comprising 6 M urea, 0.01 M sodium citrate, pH 4.8 until the sodium chloride present in the previous buffer was completely displaced.

The purified bound vWF fraction was finally washed with a buffer comprising 6 M urea, 0.01 M citric acid, pH 3.0 causing an additional small amount of UV absorbing material to be eluted. Washing was continued until this material could no longer be detected. Although pH 3.0 is well below the pKa of the unoccupied column carboxyl groups, the preformed complexes between positively charged vWF fragment and negatively charged resin remain substantially intact at this pH for the indicated time. Maintenance of the vWF fragments at this low pH continues to promote further monomerization of the fragment population, with monomers and dimers being now predominant and soluble aggregate being substantially reduced. Percent monomer, dimer and aggregate may be determined according to the assay procedure of Example 2.

The recombinant vWF factor fragment was finally eluted from the CM-Sepharose® column with a pH 3.0 buffer comprising M urea and 0.2 M citric acid. The eluting peak was collected as a pool of UV absorbing fractions and filtered through a 0.2 micron filter. The eluted population of fragments represents 50% dimeric and 50% monomeric material with virtually no soluble aggregate being detected. Citrate ions at pH 3.0 are found to bear on the average a net negative charge of −0.5, having on average 2.5 protonated carboxyl groups (the $pKa_1$ of citrate is 3.08). It is believed that the citrate ions facilitate breakup of the fragment-resin complexes by competing for positively charged fragments, in effect performing the role of an additional "stationary" phase.

Eluted product was concentrated to approximately 10 mg/ml of protein by ultrafiltration. The concentrated product was again refiltered through an appropriately sized 0.2 micron disposable filter after which the material was dialyzed against 50 volumes of "formulation buffer" comprising 1 mM lysine monohydrochloride, 1.5 mM sodium chloride, 1 mM citric acid, 5% (w/v) mannitol, having a pH of 3.5. Dialysis buffer was replaced 3 times over a 2–3 day period at which point monomerization is also completed. The resultant product (containing approximately 70% monomer and 30% dimer, see Example 2) was filtered through an appropriate size 0.2 micron filter and stored at 4° C. until being vialed.

Residual DNA and endotoxin in the purified vWF solution were determined to be about 0.94 Eu/mg protein and about 0.15 pg/mg protein respectively. DNA analysis was performed by hybridization against *E.coli* DNA samples. Endotoxin was analyzed by the Limulus amebocyte lysate assay.

The sterile bulk solution was loaded into a type I flint glass vial (Wheaton Scientific, Millville, N.J.) to approximately the 4 ml volume level of a 20 ml capacity vial, after which siliconized butyl gray rubber lyophilization stoppers (West Co.) were applied to the filled vials. The vials were then placed in a vacuum lyophilizer (Hull Corporation, Hatboro, Pa.) and frozen at −42° C., after which they were exposed to a vacuum of 60 microns for 12 hours. After 12 hours, the temperature of the sample was gradually increased (over 24 hours) to approximately 30° C. This temperature and vacuum were maintained for an additional 16 hours. Atmospheric pressure was restored in the chamber using sterile dry nitrogen after which the vials were capped. The vials were stored at 4° C. until needed at which point they may be reconstituted using a 4 ml volume of pyrogen-free water.

Example 2

Demonstration that Preparations of Unaggregated Alkylated vWF Fragment Reflect an Equilibrium between Dimer and Monomer Samples of unaggregated, alkylated vWF fragment containing different total fragment concentrations were prepared according to the procedure of Example 1 and placed in standard formulation buffer (1 mM lysine monohydrochloride, 1.5 mM sodium chloride, 1 mM citric acid, 5% mannitol (w/v) at pH 3.5) and then incubated at 4° C. overnight. The samples were then applied to a column containing a crosslinked dextran gel (Sephadex® G-100, Pharmacia, Uppsala, Sweden) for chromatography based on molecular weight (size) exclusion so that the percent of monomer and of dimer together comprising the unaggregated product could be determined.

Generally, any amounts of soluble aggregate in fragment samples may be determined by detection in the void volume on a G-100 column. With respect to amounts of small aggregates (i.e. trimers, tetramers) a G-50 column can be used.

Two ml samples (1–11 mg/ml) were loaded on the 1.5×88 cm G-100 column at 4° C. Three ml eluent fractions were collected and monitored for protein concentration at 280 nm. The monomeric fragment peak was centered at approximately fraction 24 and the dimer at fraction 31.

FIG. 1 shows a plot of % monomer detected in the samples after overnight incubation in formulation buffer as a function of total mg/ml of fragment in the samples. By extrapolating from the linear range presented in FIG. 1, storage of vWF fragment at a concentration of approximately 20 mg/ml results in product which is primarily dimer. Therapeutic product which is primarily monomeric can be generated from samples having a fragment storage concentration of 2 mg/ml. A shift in the monomer/dimer equilibrium is therefore produced by lowering the concentration of unaggregated alkylated fragment in storage solutions suitable for administration to patients. Similar results were obtained whether the tested solutions were or were not reconstituted with an appropriate volume of pyrogen-free water from prior storage in lyophilized form.

Since monomeric fragment has a greater ability to inhibit platelet aggregation than dimeric fragment on a per weight basis, the therapeutic utility of vWF fragment prepared for injection in formulation buffer can be increased by storage at, or reconstitution to, a dilute concentration of fragment such as approximately 2 mg/ml. It is noted that formulation of the fragment in the preferred storage solutions of the invention provides a product in which the percent of monomer and of dimer in the product is substantially unaffected by lyophilization and rehydration.

Example 3

Effect of Aggregation on the Biological Activity of the Alkylated vWF Fragment

Botrocetin, a protein extracted from the venom of *Bothrops jararaca*, facilitates the in vitro binding of multimeric von Willebrand factor to platelets (Read, et al., *Proc. Natl. Acad. Sci. USA*, 75, 4514–4518 (1978). The binding site for botrocetin in the mature vWF subunit has been localized within the region thereof containing amino acid sequence positions 445–733, and thus the GPIb binding domain. Andrews, R. K. et al., *Biochemistry*, 28, 8317–8326 (1989). It is believed that binding of botrocetin to vWF induces in the vWF molecule a conformational change which would otherwise be induced in vivo by a signal associated with damage to the vascular system. Accordingly, the effect of aggregation of the alkylated fragment on its ability to inhibit agglutination of platelets mediated by multimeric vWF was tested in a botrocetin-triggered assay.

Unaggregated alkylated vWF fragment represents the combined concentration of the monomer and dimer. Actual percent dimer was not calculated. Reference to FIG. 1 demonstrates that samples of unaggregated alkylated von Willebrand factor fragment purified according to the procedure of Example 1 contain, if stored in formulation buffer at between 2 and 8 mg/ml, approximately 70% of monomer and 30% of dimeric alkylated von Willebrand factor fragment. The dimeric fragment is about one-half as effective, on a per weight basis, as the monomer in inhibiting platelet agglutination, although the dimer is as fully soluble as the monomer under the conditions utilized in the assays of this Example.

Inhibition of agglutination by alkylated fragment was therefore measured as a function of monomer and dimer concentration (from preparations containing no aggregated material) and was compared with the response provided by aggregated preparations. The agglutination protocol was adapted from the procedure of Brinkhous, K. M. and Read, M. S., *Blood,* 55(3), 517–520 (1980) and Fugimura, et al., *J. Biol. Chem.,* 261,381–385 (1986) .

In this assay, specific amounts of botrocetin and multimeric vWF were used to agglutinate (aggregate) a specified amount of platelets thereby defining a reference value of 100% aggregation. Specific amounts of alkylated vWF fragment were used to create reaction mixtures comprising also multisubunit vWF, botrocetin, and platelets, so that the $IC_{50}$ (concentration of vWF fragment effective to inhibit 50% of botrocetin-induced platelet agglutination) could be determined.

Platelets for the assay were prepared using a gel filtration technique according to the procedure of Marguerie, et al., *J. Biol. Chem.,* 254, 5357–5363 (1979), and then fixed following a modified form of the procedure of Allain, et al., *J. Lab. Clin. Med.,* 85, 318–328 (1975), said modifications comprising: (1) applying as fixative 0.5% paraformaldehyde; (2) after which fixation was accomplished in 30 minutes at room temperature. In addition, the platelets were treated to make inoperative the glycoprotein IIb/IIIa receptor sites by treating (for 30 minutes at 37° C.) a suspension of the platelets with 5 mM EDTA at pH 8.5 causing dissociation of the intact IIb/IIIa receptor complexes. Inhibition of platelet agglutination (aggregation) was monitored in siliconized glass cuvettes maintained at 37° C. with constant stirring (1000 rpm) in a Platelet Aggregation Profiler, Model PAP-4 (Bio-Data Co., Hatboro, Pa.) operated according to instructions supplied by the manufacturer.

Figure 2:
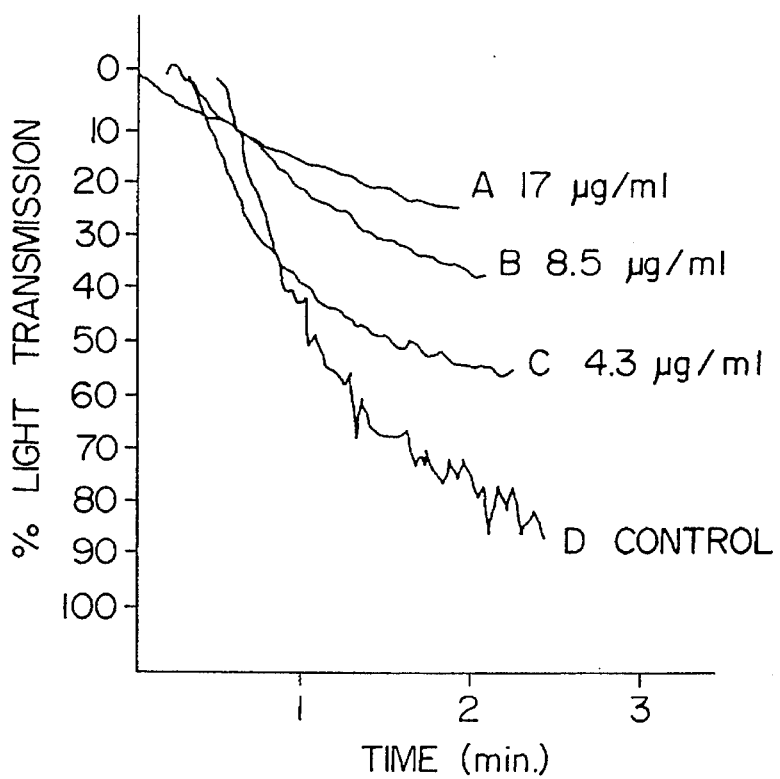
FIG. 2 is a recording of the inhibition of platelet agglutination (aggregation) caused by specified concentrations of alkylated von Willebrand factor fragment.

Assays were performed as follows. Assay components were kept on ice prior to use at 37° C. in the assay incubations. To begin the assay, 0.4 ml of fixed human platelets ($2 \times 10^8$ ml) was added to the cuvette and incubated at 37° C. for 4 minutes. A small µl quantity of vWF fragment dissolved in formulation buffer (containing also 0.1% human serum albumin) or an equivalent volume of formulation buffer-HSA (for a control) was then added to the cuvette for one minute of incubation at 37° C. With respect to the agglutination profiles presented in FIG. 2, a 30 µl formulation buffer-HSA sample was used as control and 30 µl quantities of serial dilutions of purified alkylated fragment (resulting in 17.0, 8.5 and 4.3 µg/ml final assay concentrations of fragment) were used. Multimeric native vWF, prepared according to the method of Newman, et al., *Br. J. Hematol.,* 21, 1–20 (1971), was then added to each cuvette and incubated at 37° C. for one minute. An appropriate aliquot of vWF was added to the reaction mixture to provide a final vWF concentration of 6.3 µg/ml. Finally, 12.5 µl of an appropriately concentrated botrocetin solution (purified according to the procedure of Read, et al., *Proc. Natl. Acad. Sci. USA,* 75, 4514–4518 (1978)) was added to provide a final concentration of botrocetin of 8.2 µg/ml in the reaction mixture, which was then incubated for a final one minute at 37° C. The agglutination reaction was then monitored over a two minute period. As demonstrated in FIG. 2, the purified and unaggregated alkylated vWF fragment (representing a population of approximately 70% monomer/30% dimer) is effective in a dose dependent fashion as an inhibitor of platelet aggregation.

Figure 3:
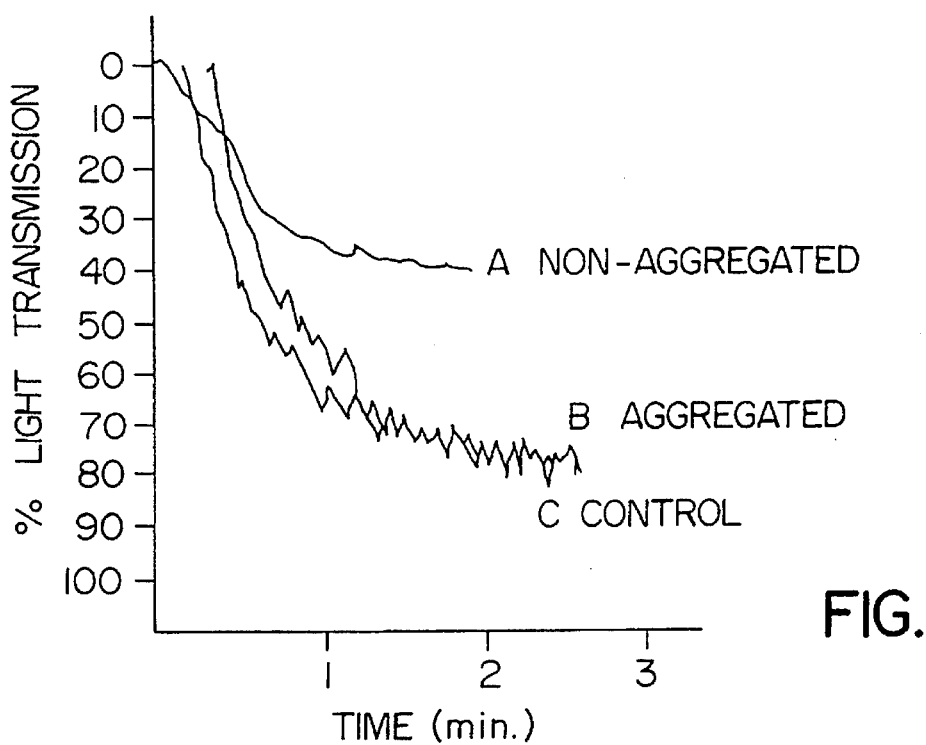
FIG. 3 is a recording of the comparative ability of non-aggregated and aggregated alkylated von Willebrand factor fragment to inhibit platelet agglutination.

FIG. 3 presents a similar experiment in which the unaggregated fragment (comprising approximately 70% monomer/30% dimer) was compared with aggregated fragment material for potency of agglutination inhibition. The assays were performed as above using 30 µl quantities of vWF fragment of a concentration providing 7.3 µg/ml as the final concentration of potentially agglutination-inhibiting material. The unaggregated material was substantially effective in inhibiting platelet agglutination whereas the aggregated vWF-derived material was not. Reference to FIG. 3 shows that under the assay conditions of this Example, 50% of inhibition of agglutination is obtained at a fragment concentration ($IC_{50}$) of approximately 7.3 µg/ml of unaggregated material (equivalent to 0.22 µM thereof) whereas the aggregated form exhibits no more than 5% inhibititory effect under these conditions.

EXAMPLE 4

Effect of Combined α-Helical and β-sheet content on the solubility of Unaggregated Alkylated vWF Fragment FIG. 4 shows a comparison of the circular dichroism profile of alkylated vWF fragment (at pH 3.5 versus 4.5) in a solution comprising standard formulation buffer without mannitol. Spectra were produced for identically concentrated samples at 25° C. in a Jasco, Inc. (Easton, Md.) model 500A spectrophotometer by scanning down from approximately 350 nm.

The spectrum of the alkylated fragment could not be determined in 1 mM phosphate buffer, pH 7.5 because of precipitation of the fragment. The respective contributions of component α-helix, β-pleated sheet and random coil regions to the total rotation near 222 nm were not determined; however, it is clear that the alkylated fragment possesses a more ordered structure at pH 3.5 than at 4.5.

Deposit of Strains Useful in Practicing the Invention

Deposits of biologically pure cultures of the following strains were made under the Budapest Treaty with the American Type Culture Collection, 12301 Parklawn Drive, Rockville, Md. The accession numbers indicated were assigned after successful viability testing, and the requisite fees were paid.

Access to said cultures will be available during pendency of the patent application to one determined by the Commissioner of the United States Patent and Trademark Office to be entitled thereto under 37 C.F.R. §1.14 and 35 U.S.C. §122, or if and when such access is required by the Budapest Treaty. All restriction on availability of said cultures to the public will be irrevocably removed upon the granting of a patent based upon the application and said cultures will remain permanently available for a term of at least five years after the most recent request for the furnishing of samples and in any case for a period of at least 30 years after the date of the deposits. Should the cultures become nonviable or be inadvertantly destroyed, they will be replaced with viable culture(s) of the same taxonomic description.

| Strain/Plasmid | ATCC No. | Deposit Date |
| --- | --- | --- |
| BL21(DE3) pLysS/pET-8c52K(Km$^R$) | 68306 | April 17, 1990 |

We claim:

1. A process for preparing an aqueous solution of cysteine-altered von Willsbrand factor (vWF) fragment which has a molecular weight of approximately 33,000, an amino terminal residue at about amino acid residue 449 and a carboxy terminal residue at about amino acid residue 728, and which is substantially free of aggregate comprising the sequential steps of:

(A) providing an aqueous solution of denaturant and recombinantly prepared, cystsine-altered vWF fragments which are based on human vWF, the fragments tending to aggregate in the absence of the denaturant;

(B) purifying the aqueous solution of fragment and denaturant under conditions which promote conversion of aggregated forms of the fragment to the dimeric and/or monomeric forms thereof to provide dissolved purified fragment; and (C) separating the dissolved, purified fragment from the denaturant while maintaining the aqueous solution of the fragment at a pH of about 2.5 to less than about 5.5 to increase monomerization of, and decrease aggregation of, said fragment, thereby forming an aqueous solution of cystsine-altered vWF fragment which is substantially free of aggregate.

2. A process according to claim 1 wherein the source of said fragment is a fragment prepared by subjecting an aqueous solution of the recombinant vWF fragment and denaturant to alkylating conditions, thereby forming an alkylated vWF fragment.

3. A process according to claim 2 wherein the solution of step (B) has an alkaline pH and contains bacterial contaminants and including the steps of:

(D) separating contaminants from said solution by contacting said solution having an alkaline pH with an anionic exchange material to which contaminants adhere;

(E) contacting the aqueous solution from which contaminants have been removed with a cationic exchange resin to which the fragment adheres; and (F) eluting the fragment from the cationic exchange resin by contacting the resin with an aqueous solution containing ionized citric acid and a nonionic denaturant wherein affinity of the eluted fragment for citrate ions of said aqueous solution containing ionized citric acid facilitates solubilization from said cationic exchange resin.

4. A process according to claim 1 including freezing or lyophilizing said solution which is substantially free of aggregate.

5. A process according to claim 1 wherein said pH is maintained at about 3 to about 4.

6. A process according to claim 2 wherein said alkylating conditions include the use of iodocetamide as the alkylating agent.

7. A process according to claim 1 wherein the denaturant referred to in each of steps (A) and (B) is urea.

8. A process according to claim 1 wherein said denaturant is an aqueous solution of urea and said vWF fragment is produced by a bacterial host cell.

9. A process according to claim 8 wherein the cysteine-altered form of the fragment is an alkylated vWF fragment.

10. A process according to claim 9 wherein the solution of step (B) has an alkaline pH and contains bacterial contaminants and including the steps of:

(D) separating contaminants from said solution by contacting said solution having an alkaline pH with an anionic exchange material to which contaminants adhere;

(E) contacting the aqueous solution from which contaminants have been removed with a cationic exchange resin to which the fragment adheres; and (F) eluting the fragment from the cationic exchange resin by contacting the resin with an aqueous solution containing ionized citric acid and a nonionic denaturant, wherein affinity of the eluted fragment for citrate ions of said aqueous solution containing ionized citric acid facilitates solubilization from said cationic exchange resin.

11. A process according to claim 8 wherein said pH is maintained at about 3 to about 4.

12. A process according to claim 1 wherein said aqueous solution of the fragment at a pH of about 2.5 to less than about 5.5 includes therein about 1 to about 30 mg/ml of said fragment.

13. A process according to claim 1 wherein said aqueous solution of the fragment at a pH of about 2.5 to less than about 5.5 includes a total concentration in the solution of ions less than about 75 mM.

14. A process according to claim 1 wherein said aqueous solution of the fragment at a pH of about 2.5 to less than about 5.5 includes about 1 to about 10 mg/ml of said fragment and wherein the total concentration in the solution of ions is less than about 75 mM.

15. A process for limiting dimerization of monomeric von Willsbrand factor (vWF) fragment having a molecular weight of approximately 33,000, an amino terminal residue at about amino acid residue 449, and a carboxy terminal residue at about amino acid residue 728, said fragment being based on human vWF and prepared by recombinant means and in cystsine-altered form, said dimerization involving one or more of ionic, hydrophobic or hydrogen bonds which facilitate in vivo the association of two or more mature vWF subunits, said process comprising forming an aqueous solution of monomeric cystsine-altered vWF fragment which has a pH of about 2.5 to less than about 5.5 and which includes therein up to about 10 mg/ml of said fragment and wherein the total concentration in the solution of additional species of ions (if any) is less than about 75 mM.

16. A process according to claim 15 wherein the fragment is produced by a bacterial host cell.

17. A process according to claim 1 wherein the cystsine-altered von Willsbrand factor (vWF) fragment has an amino terminal residue at amino acid residue 445 and a carboxy terminal residue at amino acid residue 733.

18. A process according to claim 15 wherein the monomeric von Willebrand factor (vwF) fragment has an amino terminal residue at amino acid residue 445 and a carboxy terminal residue at amino acid residue 733.

* * * * *